United States Patent
Li et al.

(10) Patent No.: US 10,452,948 B2
(45) Date of Patent: Oct. 22, 2019

(54) OBJECT IDENTIFICATION METHOD IN DUAL-ENERGY CT SCAN IMAGES

(71) Applicant: GENERAL ELECTRIC COMPANY, Schenectady, NY (US)

(72) Inventors: Jianying Li, Beijing (CN); Shuo Li, Beijing (CN); Zhihui Sun, Beijing (CN); Zhi Ye, Beijing (CN); XiaoYan Yu, Beijing (CN); Ke Sun, Beijing (CN)

(73) Assignee: General Electric Company, Schenectady, NY (US)

( * ) Notice: Subject to any disclaimer, the term of this patent is extended or adjusted under 35 U.S.C. 154(b) by 50 days.

(21) Appl. No.: 14/548,848

(22) Filed: Nov. 20, 2014

(65) Prior Publication Data
US 2015/0161787 A1 Jun. 11, 2015

(30) Foreign Application Priority Data
Dec. 9, 2013 (CN) .......................... 2013 1 0660019

(51) Int. Cl.
*G06K 9/60* (2006.01)
*A61B 6/00* (2006.01)
(Continued)

(52) U.S. Cl.
CPC ................ *G06K 9/60* (2013.01); *A61B 6/481* (2013.01); *A61B 6/482* (2013.01); *A61B 6/5217* (2013.01); *G06T 7/11* (2017.01); *G06T 7/174* (2017.01); *G06T 2207/10081* (2013.01); *G06T 2207/30101* (2013.01)

(58) Field of Classification Search
None
See application file for complete search history.

(56) References Cited

U.S. PATENT DOCUMENTS 8,055,050 B2 11/2011 Roessl et al.
8,294,717 B2 * 10/2012 Zamyatin et al. ............ 345/440
(Continued)

FOREIGN PATENT DOCUMENTS

CN 1940992 A 4/2007
JP 2004-174253 A 6/2004
(Continued)

OTHER PUBLICATIONS

Wang X, Meier D, Taguchi K, Wagenaar DJ, Patt BE, Frey EC. Material separation in x-ray CT with energy resolved photon-counting detectors. Med Phys. 2011;38(3):1534-46.*
(Continued)

*Primary Examiner* — Jiangeng Sun
(74) *Attorney, Agent, or Firm* — McCoy Russell LLP

(57) ABSTRACT

A method is provided for processing a dual-energy CT scan image, which includes filtering the pixels in a dual-energy CT scan image to obtain pixels to be grouped; grouping the pixels to be grouped into a plurality of pixel groups based on the positions of the pixels to be grouped in the dual-energy CT scan image; performing material decomposition on the pixels in each pixel group; and determining the object corresponding to each pixel group based on the results of material decomposition. By using the method, the scan time and the X-ray dose radiated to a target (e.g., a user to be diagnosed) are reduced.

16 Claims, 4 Drawing Sheets

(51) Int. Cl.
*G06T 7/11* (2017.01)
*G06T 7/174* (2017.01)

(56) References Cited

U.S. PATENT DOCUMENTS

| | | | |
|---|---|---|---|
| 8,837,677 B2 * | 9/2014 | Boyden et al. | 378/87 |
| 2004/0101086 A1 | 5/2004 | Sabol et al. | |
| 2006/0285737 A1 * | 12/2006 | Hamill et al. | 382/131 |
| 2007/0030944 A1 | 2/2007 | Grasruck et al. | |

FOREIGN PATENT DOCUMENTS

| | | |
|---|---|---|
| JP | 2004-174261 A | 6/2004 |
| JP | 2007-044520 A | 2/2007 |
| JP | 2007-111525 A | 5/2007 |
| JP | 2009-142518 A | 7/2009 |
| JP | 2010500901 A | 1/2010 |
| WO | WO 2004098649 A2 * 11/2004 ............. A61K 49/00 |

OTHER PUBLICATIONS

OriginLab, "interpreting Regression Results", 2012. Retrieved from the Internet: <URL: http://coen.boisestate.edu/bknowlton/files/2011/09/Interpreting-Regression-Origin-Labs.pdf>.*

Machine Translation and Notification of Reasons for Refusal issued in connection with corresponding JP Application No. 2014-246381 dated Apr. 3, 2018.

Machine Translation and First Office Action and Search issued in connection with corresponding CN Application No. 201310660019.4 dated May 18, 2018.

Japanese Patent Office, Decision to Grant a Patent Issued in Application No. 2014-246381, dated Oct. 23, 2018, 5 pages. (Submitted with Machine Translation).

* cited by examiner

OBJECT IDENTIFICATION METHOD IN DUAL-ENERGY CT SCAN IMAGES

BACKGROUND

Embodiments of the present invention relate generally to the field of computerized tomography (CT) and, more specifically, to an object identification method in dual-energy CT scan images.

Scan images of a target object obtained through computerized tomography (CT) technology include a plurality of pixels of different gray scales. The gray scales of the pixels are proportional to the density of the target object to be scanned. Areas of different densities in the target to be scanned differ in terms of the level of X-ray absorption. Therefore, in a CT scan image, pixels having a low gray scale are used to represent low density area having a lower X-ray absorption level, and pixels having a higher gray scale are used to represent high density area having a higher X-ray absorption level. Usually, a CT value (unit: Hu) is used to represent the pixels in a CT scan image. For example, the CT value of pixels corresponding to an object or tissue with a higher level of X-ray absorption is set to be higher than the CT value of pixels corresponding to an object or tissue with a lower level of X-ray absorption. For example, the CT value of pixels corresponding to bone tissue is set as +1000 Hu, the CT value of pixels corresponding to water is set as 0 Hu, the CT value of pixels corresponding to the air is set as −1000 Hu, and so on.

Currently, a dual-energy CT technology has been has proposed. In this technology, X-rays of two different energies are used to scan the target to be scanned, thereby obtaining a dual-energy CT scan image of the target. Such a dual-energy CT scan image contains more information than the scan image obtained by using the traditional single-energy CT technology employing single energy X-rays to scan the target.

However, in both single-energy CT scan images and dual-energy CT scan images, different objects in the target may have the same or similar levels of X-ray absorption. For example, the bone tissue and the calcified part such as blood vessels or other tissues developed due to lesions may have the same or similar X-ray absorption level, and hence the same or similar CT value. Therefore, it is difficult to distinguish objects represented by pixels of the same or similar grayscale values in a CT scan image.

In addition, in order to highlight the different objects in the target, a contrast agent is applied (e.g., injected) to the target before performing a CT scan. The CT scan where a contrast agent is applied to the object is also called a CT contrast enhanced scan, and the CT scan images obtained thereof are also called CT contrast enhanced scan images.

However, in the CT contrast enhanced scan images, because the pixels corresponding to the contrast agent have a relatively high CT value, it is difficult to distinguish the pixels corresponding to the contrast agent from pixels corresponding to bone tissue or other tissues that have a relatively high density and relatively high X-ray absorption level. In the prior art, there is a method for identifying pixels corresponding to the contrast agent by comparing the CT scan images (unenhanced images) obtained by a CT scan before applying the contrast agent (unenhanced scan) with the CT contrast enhanced scan images (enhanced image). However, such method requires two CT scans of the target, and thus increases the X-ray absorption dose by the target.

Therefore, there is a need for a method for identifying different objects in a CT scan image.

SUMMARY

The purpose of the exemplary embodiments of the present invention is to overcome the above and/or other problems in the prior art. Therefore, exemplary embodiments of the present invention provide a method for processing a dual-energy CT scan image in which different objects can be easily distinguished.

According to an exemplary embodiment of the present invention, there is provided a method for identifying a contrast agent in a dual-energy CT contrast enhanced scan image, the method including: filtering pixels in the dual-energy CT contrast enhanced scan image to obtain pixels to be grouped; grouping the pixels to be grouped into a plurality of pixel groups based on positions of the pixels to be grouped in the dual-energy CT contrast enhanced scan image; performing material decomposition on the pixels in each pixel group; and determining the pixel group corresponding to the contrast agent in the plurality of pixel groups based on results of material decomposition.

According to an exemplary embodiment of the present invention, there is provided a method for processing a dual-energy CT scan image, the method including filtering pixels in the dual-energy CT scan image to obtain pixels to be grouped; grouping the pixels to be grouped into a plurality of pixel groups based on positions of the pixels to be grouped in the dual-energy CT scan image; performing material decomposition on the pixels in each pixel group; and determining the object corresponding to each pixel group based on results of material decomposition.

BRIEF DESCRIPTION

The present invention will be better understood by the following description of the exemplary embodiments of the present invention with reference to the accompanying drawings, wherein.

DETAILED DESCRIPTION

In the following detailed description, embodiments of the present invention will be described. It shall be noted that in the detailed description of these embodiments, for the sake of conciseness, not all features in the practical implementation modes are described in detail. It will be understood that in the actual implementation of an implementation mode, as in any engineering or design project, in order to achieve the developers' specific goals and to meet system-related or business-related constraints, a variety of specific decisions will be made so that the embodiments implemented will vary from one to another. In addition, it will also be understood that, although the efforts made in the process of such development might be complex and lengthy, for those having ordinary skills in the field relating to the disclosure of the present invention, designs and variations of the manufacture or production made on the basis of the technical contents disclosed in this disclosure merely pertain to conventional technical means and shall not be deemed as insufficient disclosure.

Unless otherwise defined, the technical terms or scientific terminologies as used in the claims and description should be interpreted as having the meaning generally understood by those having ordinary skills in the art. In the description and claims, terms like "first", "second", and so on are not intended to denote any order, quantity, or importance, but are merely used to distinguish between different components. Terms like "a", "an", and so on do not impart any quantitative restrictions, but rather indicate the presence of at least one. Terms like "comprise", "include", and so on do not exclude other elements or objects that are not listed following said terms. Terms like "connect", "connection", and so on are not limited to physical or mechanical connections, or to direct or indirect connections.

Figure 1:
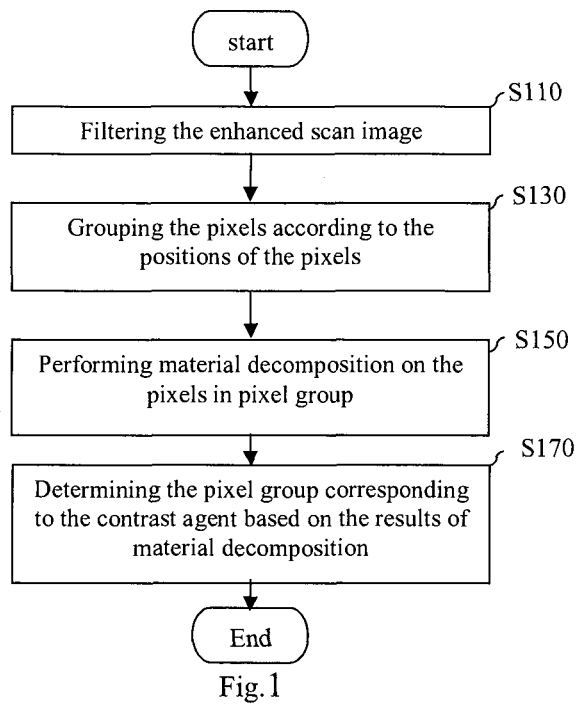
FIG. 1 is a flow chart of a contrast agent identification method in a dual-energy CT contrast enhanced scan image according to an exemplary embodiment.

FIG. 1 is a flow chart of a contrast agent identification method in a dual-energy CT contrast enhanced scan image according to an exemplary embodiment.

Figure 2:
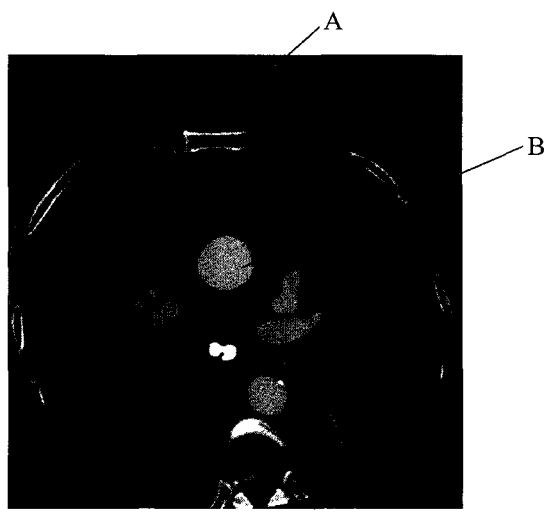
FIG. 2 shows an example of a dual-energy CT contrast enhanced scan image according to an exemplary embodiment.

As shown in FIG. 1, at step S110, the dual-energy CT contrast enhanced scan image of a target (e.g., a user to be diagnosed) may be filtered. FIG. 2 shows an example of a dual-energy CT contrast enhanced scan image according to an exemplary embodiment. In performing image filtering, a determination can be made as to whether the CT values of the pixels in the dual-energy CT contrast enhanced scan image as shown in FIG. 2 are greater than a reference CT value, and the pixels with CT values greater than the reference CT value can be determined as filtered pixels. Because the filtered pixels will be subsequently grouped (which will be described in detail below), the filtered pixels can also be referred to as pixels to be grouped. Here, the reference CT value may be a preselected value. In the current exemplary embodiment, in order to distinguish pixels corresponding to the contrast agent from those corresponding to other objects such as the bone tissue, the reference CT value may be selected as 100 Hu. However, it shall be understood that the exemplary embodiment is not limited thereto, and the dual-energy CT contrast enhanced scan image can be filtered using different reference CT values. For example, the pixels with CT values smaller than the reference CT value may be regarded as the pixels to be grouped, or the pixels with CT values greater than a first reference CT value and smaller than a second reference CT value may be regarded as the pixels to be grouped (the first reference CT value being smaller than the second reference CT value).

Figure 3:
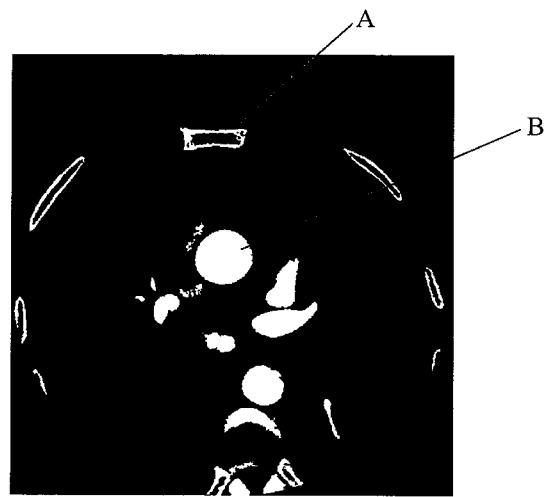
FIG. 3 shows an example of a filtered scan image according to an exemplary embodiment.

FIG. 3 shows an example of a filtered scan image according to an exemplary embodiment.

After the dual-energy CT contrast enhanced scan image as shown in FIG. 2 has been filtered using a reference CT value which is 100 Hu, a filtered scan image that merely includes the pixels to be grouped can be obtained, as shown in FIG. 3. In FIG. 3, part A may be the pixels corresponding to the bone tissue, and part B may be the pixels corresponding to the contrast agent (such as the contrast agent contained in the blood).

Referring back to FIG. 1, after the dual-energy CT contrast enhanced scan image has been filtered, the resulting pixels to be grouped may be grouped (S130). The pixels to be grouped may be automatically or manually grouped into a plurality of pixel groups based on the positions of the pixels to be grouped in the dual-energy CT contrast enhanced scan image. For example, in the case of automatic grouping, a pixel to be grouped can be selected (for example, arbitrarily selected) first, and then a pixel of the pixels to be grouped adjacent to said selected pixel can be grouped into the same group as the selected pixel. The process can repeat until all the pixels to be grouped are grouped into corresponding pixel groups. In this way, positionally adjacent pixels in the pixels to be grouped can be automatically grouped into the same pixel group.

Referring to FIG. 1, after the pixels to be grouped have been grouped, the pixels in each of the pixel groups can be subjected to material decomposition (S150). Because a dual-energy CT scan image can provide more information than a single-energy CT scan image, the material decomposition can be performed such that at least two decomposition values can be obtained for each pixel. Here, the two decomposition values of each pixel can be respectively equivalent density values of two different basis materials or CT values corresponding to two different energies used for performing the dual-energy CT scan. In the following, an exemplary embodiment where the two decomposition values of each pixel are respectively the equivalent density value of water and the equivalent density value of iodine contained in the contrast agent will be described.

As shown in FIG. 1, after material decomposition of the CT values of the pixels in each pixel group, pixel groups in the plurality of pixel groups that correspond to objects other than the target (e.g., bone tissue, contrast agent, etc) can be determined based on the results of material decomposition (S170).

Figure 4:
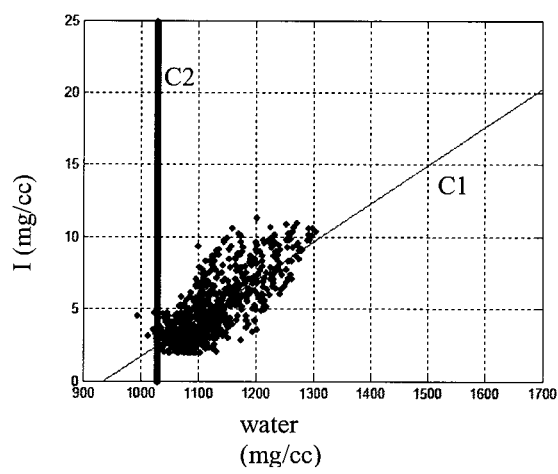
FIGS. 4 and 5 show examples of decomposition scatter diagrams corresponding to different pixel groups according to an exemplary embodiment.
Figure 5:
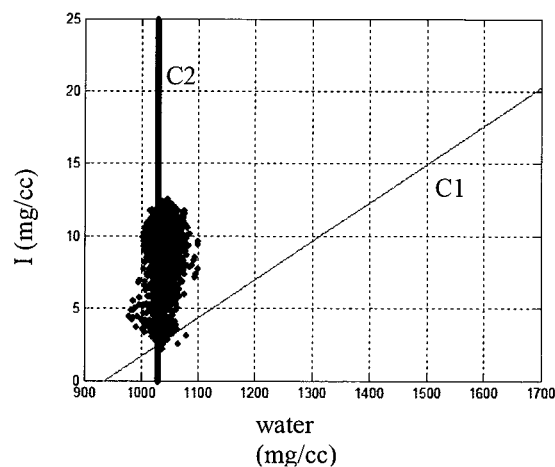

For example, a decomposition value scatter diagram indicating the relationship between the two decomposition values of each pixel in a pixel group can be established based on the decomposition values of the pixels in each pixel group. FIGS. 4 and 5 show examples of decomposition scatter diagrams corresponding to different pixel groups according to an exemplary embodiment, wherein FIG. 4 is the decomposition scatter diagram of the pixel group corresponding to part A (group A) in FIG. 2 and FIG. 5 is the decomposition scatter diagram of the pixel group corresponding to part B (group B) in FIG. 2.

Because group A and group B represent different objects (namely, the bone tissue and the contrast agent respectively), in the decomposition scatter diagram the distribution of the pixels in group A can be different from the distribution of the pixels in group B, as shown FIGS. 4 and 5. Therefore, the object corresponding to each pixel group can be determined manually or automatically based on the positions of the pixels of the pixel group in the decomposition scatter diagram (S170).

For example, in the case of automatically determining the object corresponding to each pixel group, a calculation can be made as to the average distances between positions of the pixels of a pixel group in the decomposition value scatter diagram and characteristics curves representing different objects, and if the average distance between the former and a particular characteristics curve is less than or equal to a reference value, said pixel group can be determined as corresponding to the object represented by said characteristics curve. Such characteristics curves and reference value can be determined beforehand. However, it shall be understood that the exemplary embodiment is not limited thereto. In other exemplary embodiments, a calculation can be made as to an average distance between positions of the pixels of a pixel group in the decomposition value scatter diagram and a characteristics curve (e.g., a contrast agent characteristics curve) representing a particular object (e.g., a contrast agent), and an average distance between positions of the pixels of the pixel group in the decomposition value scatter diagram and a characteristics curve of an object other than the particular object (e.g., a contrast agent) in the dual-energy CT contrast enhanced scan image. If the average distance between positions of the pixels of the pixel group in the decomposition value scatter diagram and the characteristics curve of said particular object (e.g., a contrast agent) is less than the average distance between positions of the pixels of the pixel group in the decomposition value scatter diagram and the characteristics curves representing other objects, the pixel group can be determined as corresponding to the particular object (e.g., a contrast agent).

FIGS. 4 and 5 show examples of the characteristics curve C1 representing the bone tissue and the characteristics curve C2 representing the contrast agent. As shown in FIG. 4, the average distance between the pixels in group A and the characteristics curve C1 representing the bone tissue may be less than the reference value, and the average distance between the pixels in group A and the characteristics curve C2 representing the contrast agent may be greater than the reference value. Therefore, group A can be determined as corresponding to the bone tissue. As shown in FIG. 5, the average distance between the pixels in group B and the characteristics curve C1 representing the bone tissue may be greater than the reference value, and the average distance between the pixels in group B and the characteristics curve C2 representing the contrast agent may be less than the reference value. Therefore, group B can be determined as corresponding to the contrast agent.

Alternatively, because the average distance between the pixels in group A and the characteristics curve C1 representing the bone tissue can be smaller as compared to the average distance between the pixels in group A and the characteristics curve C2 representing the contrast agent, the pixels in group A can be determined as corresponding to the bone tissue. Similarly, because the average distance between the pixels in group B and the characteristics curve C2 representing the contrast agent can be smaller as compared to the average distance between the pixels in group B and the characteristics curve C1 representing the bone tissue, the pixels in group B can be determined as corresponding to the contrast agent.

Therefore, according to the exemplary embodiments, it is possible to automatically or manually distinguish and identify different objects in a dual-energy CT scan image. For example, it is possible to accurately identify the contrast agent in a dual-energy CT contrast enhanced scan image.

In addition, in optional exemplary embodiments, after the object corresponding to a pixel group has been determined, the CT values of the pixels in a dual-energy CT scan image can be changed. For example, a pixel group corresponding to a particular object (e.g., a contrast agent) can be selected from the plurality of pixel groups and the CT values of the pixels in said selected pixel group (e.g., corresponding to the contrast agent) can be reduced. In one exemplary embodiment, the CT values of the pixels can be reduced in such a manner, namely, when the equivalent density of iodine, as one of the two decomposition values, of the pixels in the selected pixel group (for example, one corresponding to the contrast agent) is greater than, for example, 2 mg/cc, then the value can be replaced by 2 mg/cc.

Figure 6:
FIG. 6 shows an example of a processed scan image that includes pixels of reduced CT values according to an exemplary embodiment.

FIG. 6 shows an example of a processed scan image which includes pixels of reduced CT values according to an exemplary embodiment. As shown in FIG. 6, the gray scale of the pixels in Area B that has been determined as corresponding to the contrast agent is reduced due to the reduction of the CT values. Thus, in the processed image shown in FIG. 6, Area B, which corresponds to the contrast agent, is no longer highlighted, and only Area A, which corresponds to the bone tissue, is highlighted. In other words, through the above processing, it is possible to obtain a non-contrast enhanced scan image (an unenhanced scan image). In other words, it is possible to obtain an unenhanced scan image based on a dual-energy CT contrast enhanced scan image (enhanced scan image). Therefore, it is possible to obtain an enhanced scan image and an unenhanced scan image by performing a dual-energy CT contrast enhanced scan on the target only once. As such, the scan time and the X-ray dose radiated to the target (e.g., a user to be diagnosed) are reduced.

Although the obtaining of an unenhanced scan image based on a contrast enhanced scan image has been described above, it will be understood that the exemplary embodiments of the present invention are not limited thereto. As will be described below, in another exemplary embodiment, it is possible to identify different objects in a dual-energy CT scan image and to process the dual-energy CT scan image based on the results of identification.

Figure 7:
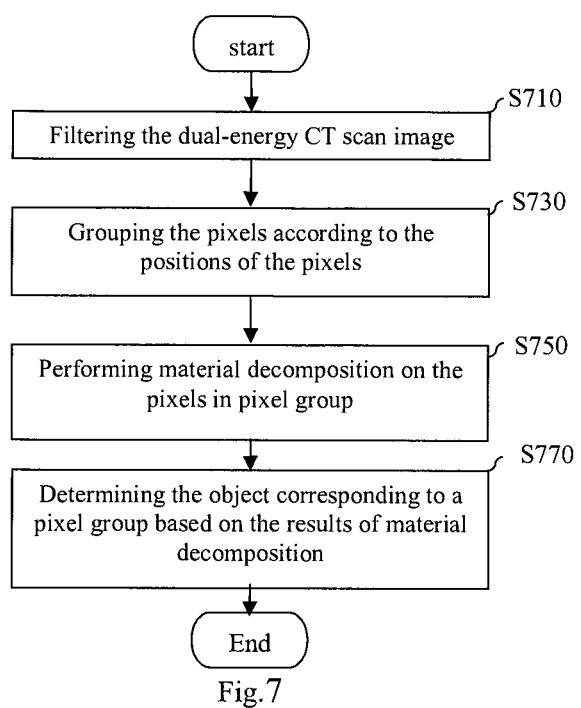
FIG. 7 shows a flow chart of an object identification method in a dual-energy CT scan image according to another exemplary embodiment.

FIG. 7 shows a flow chart of an object identification method in a dual-energy CT scan image according to another exemplary embodiment. In this embodiment, elements or features identical or similar to those in the above exemplary embodiment will not be described to avoid repetition.

Firstly, the pixels in the dual-energy CT scan image can be filtered to obtain pixels to be grouped (S710). For example, the CT values of the pixels can be compared to a reference CT value and those pixels having CT values greater than the reference CT value can be determined as the pixels to be grouped.

Then, the pixels to be grouped may be automatically or manually grouped into a plurality of pixel groups based on the positions of the pixels to be grouped in the dual-energy CT scan image (S730). For example, in the case of automatic grouping, positionally adjacent pixels in the pixels to be grouped can be grouped into the same group.

Next, the pixels in each pixel group can be subjected to material decomposition (S750). The results of material decomposition of the pixels can be equivalent density values of two different basis materials, or CT values corresponding to two different energies used for performing the dual-energy CT scan.

Then, the object corresponding to each pixel group can be automatically or manually determined based on the decomposition results of the pixels in each pixel group (S770). For example, a decomposition value scatter diagram indicating the relationship between the material decomposition results of each pixel in the pixel group can be established, and then the object corresponding to the pixel group can be determined automatically or manually based on the positions of the pixels of the pixel group in the decomposition value scatter diagram. In the case of automatically determining the object corresponding to the pixel group, a calculation can be made as to the average distances between positions of the pixels of a pixel group in the decomposition value scatter diagram and characteristics curves representing different objects, and the object represented by the characteristics curve having the minimum average distance may be determined as the object corresponding to said pixel group. Alternatively, a calculation can be made as to the average distances between positions of the pixels of a pixel group in the decomposition value scatter diagram and characteristics curves representing different objects, and if the average distance between the pixels of a pixel group and a characteristics curve representing particular object is less than or equal to a reference value, said pixel group can be determined as corresponding to the object. Here, the characteristics curves representing different objects may include characteristics curves representing bone tissue, contrast agent or other objects.

In addition, in optional exemplary embodiments, the CT values of the pixels in a dual-energy CT scan image can be changed according to the determination results of the object corresponding to each pixel group. For example, a pixel group corresponding to a particular object can be selected from the plurality of pixel groups and the CT values of the pixels in said selected pixel group can be changed. In one exemplary embodiment, the CT values of the pixels in the selected pixel group can be reduced.

According to an exemplary embodiment, it is possible to identify the pixels corresponding to each object in a dual-energy CT scan image, and thereby to change the CT values of the pixels corresponding to the contrast agent. Therefore, the gray scale of the pixels corresponding to each object in a dual-energy CT scan image can be changed as desired. As such, it is possible to obtain an image with different objects respectively highlighted by performing a dual-energy CT scan on the target only once, thereby reducing the scan time and the X-ray dose radiated to the target (e.g., a user to be diagnosed).

Although exemplary embodiments of the present invention have been described above, it shall be appreciated that various modifications can be made. For example, it will be understood that if the technique described is implemented in a different order and/or if components in the system, architecture, apparatus, or circuit described are combined in a different manner and/or replaced or supplemented by other components or equivalents, an appropriate result will be achieved. Accordingly, other implementing modes also fall within the protection scope of the claims.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method for identifying a contrast agent in a dual-energy computerized tomography (CT) contrast enhanced scan image, wherein the method comprises:
   filtering pixels in the dual-energy CT contrast enhanced scan image to obtain pixels to be grouped;
   grouping the pixels to be grouped into a plurality of pixel groups based on positions of the pixels to be grouped in the dual-energy CT contrast enhanced scan image;
   performing material decomposition of the pixels in each pixel group;
   mapping respective material decomposition scatter diagrams of the pixels in each pixel group based on the material decomposition, each material decomposition scatter diagram indicating, for each pixel, a relationship between two decomposition values of the material decomposition and including a plurality of characteristics curves, where a respective material decomposition scatter diagram is mapped for each pixel group;
   determining a respective distance of each pixel in each pixel group from each characteristics curve plotted on each material decomposition scatter diagram, each characteristics curve associated with a different material; and
   allocating the pixels associated in each pixel group with a material corresponding to one of the characteristics curves based on the respective distances.

2. The method according to claim 1, wherein the step of filtering comprises:
   determining whether a CT value of a pixel is greater than a reference CT value; and
   identifying the pixel whose CT value is greater than the reference CT value as a pixel to be grouped.

3. The method according to claim 1, wherein the step of grouping the pixels to be grouped comprises:
   grouping positionally adjacent pixels into a same pixel group.

4. A method for identifying a contrast agent in a dual-energy computerized tomography (CT) contrast enhanced scan image, wherein the method comprises:
   filtering pixels in the dual-energy CT contrast enhanced scan image to obtain pixels to be grouped;
   grouping the pixels to be grouped into a plurality of pixel groups based on positions of the pixels to be grouped in the dual-energy CT contrast enhanced scan image;
   performing material decomposition of the pixels in each pixel group;
   establishing a material decomposition scatter diagram based on decomposition results of the pixels in each pixel group, said material decomposition scatter diagram identifying a presence of one or more objects based on the decomposition results of each pixel in each pixel group;
   comparing the material decomposition of the pixels in each pixel group with a characteristics curve associated with a material; and
   determining whether a selected pixel group of the plurality of pixel groups corresponds to the material based on positions of the pixels of the selected pixel group in the material decomposition scatter diagram relative to the characteristics curve.

5. The method according to claim 4, wherein determining whether the selected pixel group corresponds to the material further comprises:
   calculating an average distance between positions of the pixels of the selected pixel group in the material decomposition scatter diagram and the characteristics curve corresponding to the material; and
   if the calculated average distance is less than or equal to a reference value, determining said selected pixel group as corresponding to the material associated with the characteristics curve.

6. The method according to claim 1, wherein the plurality of characteristics curves includes a first characteristics curve representing bone tissue and a second characteristics curve representing a contrast agent.

7. The method according to claim 3, wherein the two decomposition values of the pixels are respectively equivalent density values of two different basis materials, or CT values corresponding to two different energies used for performing a dual-energy CT scan for obtaining the dual-energy CT contrast enhanced scan image.

8. The method according to claim 2, wherein the reference CT value is 100 HU.

9. The method according to claim 1, further comprising:
changing a CT value of a pixel group corresponding to an identified material based on results of identifying the pixel group corresponding to the identified material.

10. A method for identifying an object in a dual-energy computerized tomography (CT) scan image, wherein the method comprises:
filtering pixels in the dual-energy CT scan image to obtain pixels to be grouped;
grouping the pixels to be grouped into a plurality of pixel groups based on positions of the pixels to be grouped in the dual-energy CT scan image;
performing material decomposition on the pixels in each pixel group;
comparing the material decomposition of the pixels in each pixel group with at least two characteristics curves, wherein each characteristics curve corresponds to a single material, and wherein at least one of the at least two characteristics curves is for a single material with a Hounsfield unit (HU) greater than 0; and
determining which pixel group corresponds to the object based on results of the comparing of the material decomposition and the at least two characteristics curves, including establishing a material decomposition scatter diagram based on decomposition results of the pixels in each pixel group, said material decomposition scatter diagram indicating a relationship between the material decomposition of each pixel in each pixel group, and determining whether each pixel group corresponds to at least one of the characteristics curves based on positions of the pixels of each pixel group in the material decomposition scatter diagram.

11. The method according to claim 10, wherein the step of filtering comprises:
determining whether a CT value of a pixel is greater than a reference CT value; and
identifying the pixel whose CT value is greater than the reference CT value as a pixel to be grouped.

12. The method according to claim 10, wherein the step of grouping the pixels to be grouped comprises:
grouping positionally adjacent pixels in the pixels to be grouped into a same pixel group.

13. The method according to claim 10, wherein the step of determining which pixel group corresponds to the object comprises:
calculating average distances between the positions of the pixels of each pixel group in the material decomposition scatter diagram and each characteristics curve; and
if an average distance between positions of pixels of a selected pixel group in the material decomposition scatter diagram and a characteristics curve representing the object is less than or equal to a reference value, identifying the selected pixel group as corresponding to the object.

14. The method according to claim 10, wherein the step of determining which pixel group corresponds to the object comprises:
calculating respective average distances between the positions of the pixels of each pixel group in the material decomposition scatter diagram and each characteristics curve;
identifying that a selected pixel group corresponds to the object if a selected characteristics curve of the at least two characteristics curves that represents the object is a minimum average distance from the selected pixel group.

15. The method according to claim 12, wherein two characteristics values of the pixels are respectively equivalent density values of two different basis materials, or CT values corresponding to two different energies used for performing a dual-energy CT scan for obtaining the dual-energy CT scan image.

16. The method according to claim 10, further comprising:
changing a CT value of the pixels in the dual-energy CT scan image based on results of identifying the object corresponding to each pixel group.

* * * * *